US006221153B1

United States Patent
Castor et al.

(10) Patent No.: US 6,221,153 B1
(45) Date of Patent: Apr. 24, 2001

(54) METHOD FOR PRODUCING LARGE CRYSTALS OF COMPLEX MOLECULES

(76) Inventors: Trevor Percival Castor, 469 Mystic St., Arlington, MA (US) 02174; Matthew Albert Britz, 6451 Washington Blvd., Jersey City, NJ (US) 07310; Maury David Cosman, 59 Wood St., Woburn, MA (US) 01801; Peter Richard d'Entremont, 11 Country Club Dr., Walpole, MA (US) 02081; Glenn Thomas Hong, 18 Wachusett View Dr., Westborough, MA (US) 01581

( * ) Notice: Subject to any disclaimer, the term of this patent is extended or adjusted under 35 U.S.C. 154(b) by 0 days.

(21) Appl. No.: 09/093,642

(22) Filed: Jun. 9, 1998

(51) Int. Cl.[7] .................................. C03B 7/00; B01D 9/02
(52) U.S. Cl. ........................... 117/11; 117/68; 117/925; 117/927; 23/295 R; 23/299; 23/300
(58) Field of Search ........................... 117/11, 68, 925, 117/927; 23/295 R, 299, 300

(56) References Cited

U.S. PATENT DOCUMENTS

| 4,560,774 | * | 12/1985 | Pettit et al. ........................... 549/267 |
| 5,360,478 | * | 11/1994 | Krukonis et al. ....................... 117/68 |
| 5,440,055 | * | 8/1995 | Castor ................................... 549/510 |
| 5,560,933 | * | 8/1995 | Soon-Shiong et al. ............... 424/489 |
| 5,707,634 | * | 1/1998 | Schmitt ................................. 424/400 |
| 5,776,486 | * | 7/1998 | Castor et al. ......................... 424/450 |
| 5,803,966 | * | 9/1998 | Kulshreshtha et al. ................ 117/68 |
| 5,874,029 | * | 2/1999 | Subramaniam et al. ............... 264/12 |

FOREIGN PATENT DOCUMENTS

| 403287550 | * | 12/1991 | (JP) ............................... C07C/15/20 |
| 408154689 | * | 6/1996 | (JP) ................................. C12P/7/42 |
| WO 90/03782 | * | 4/1990 | (WO) .............................. A61K/9/14 |

* cited by examiner

Primary Examiner—Benjamin Utech
Assistant Examiner—Donald L. Champagne

(57) ABSTRACT

Compressed gases, liquefied gases, or supercritical fluids are utilized as anti-solvents in a crystal growing process for complex molecules. Crystals of the present invention exhibit greater crystal size and improved morphology over crystals obtained by conventional methods.

15 Claims, 1 Drawing Sheet

METHOD FOR PRODUCING LARGE CRYSTALS OF COMPLEX MOLECULES

FIELD OF THE INVENTION

This invention relates to methods for making highly ordered, large-sized crystals of complex natural molecules. The methods, by virtue of the nature of the crystal product, have utility in purification processes, quality control, material handling and as a tool for qualitative analysis and rational drug design. The invention features the use of critical, supercritical, or near critical fluid as an anti-solvent which is added to a solution comprising a solvent and a solute composition. The addition of the critical, supercritical or near critical fluid forces the composition to leave the solution as large-sized, highly ordered crystals.

BACKGROUND OF THE INVENTION

High quality, pure crystals are of great value for a variety of industrial and research applications. For example, a frequent problem in pharmaceutical research is the difficulty of obtaining large single crystals for X-ray structural analyses to determine molecular conformations. Crystallization is also frequently used as a method of purification in the biotechnology and pharmaceutical industries. More highly ordered crystals will typically result in a more highly purified product. Larger crystals can also impart advantages in packaging and handling operations.

Crystallization is conventionally carried out from the melt, from vapor, or from solution. The first two methods are generally restricted to materials that are thermally stable at high temperatures. Almost all biologically interesting molecules are crystallized from solution. Crystal growth from a solution involves shifting the solid versus solution equilibrium so that the solution becomes supersaturated with the substance to be crystallized. The most common methods of shifting the equilibrium are thermal and chemical. Thermally shifting the equilibrium between solid and solution relies on the temperature dependence of solubility to promote crystallization. Equilibrium of solid and solution can also be chemically shifted, by the addition of a second solvent which has good miscibility with the first solvent but in which the solute is less soluble. The addition of this secondary solvent, known as an anti-solvent, will reduce the solubility of the solute, thus causing it to precipitate.

Over the past decade, compressed gases, liquefied gases, and materials intermediate to gases and liquids known as supercritical fluids have been used as anti-solvents. A pure compound becomes critical at its critical temperature ($T_c$) and critical pressure ($P_c$). A compound becomes a supercritical fluid above its critical temperature and at its critical pressure, or above its critical pressure and at its critical temperature, or where conditions exceed both the critical temperature and pressure. These parameters are intrinsic thermodynamic properties of all sufficiently stable pure component compounds. Carbon dioxide, for example, becomes a supercritical fluid at conditions equal to or exceeding its critical temperature of 31.1° C. and its critical pressure of 72.8 atm (1,070 psig). In the supercritical region, normally gaseous compounds exhibit greatly enhanced solvation power. At a pressure of 3,000 psig (204 atm) and a temperature of 40° C., carbon dioxide has a density around 0.8 g/ml and behaves very much like a nonpolar organic solvent, with a zero dipole moment.

Compounds which are capable of forming a critical fluid undergo a transition as such compounds approach critical temperatures and pressures. Within approximately ±25% Kelvin of the critical temperature and within approximately ±25% of the critical pressure, compounds exhibit fluid density and solvation properties which approach those of critical and supercritical fluids. These compounds, under such conditions approaching critical conditions, are commonly referred to as near critical fluids.

Recently, numerous compounds showing various antineoplastic and other bioactivities have been screened and identified from plant materials, microorganisms and marine organisms. Useful compounds found by these and other screening processes often require large and pure crystals in order to efficiently conduct structural analysis. Structural analysis is often helpful to better understand the mechanisms that are responsible for their specific therapeutic efficacy. Investigation of these compounds for their bioactivities has been hampered by their low natural abundance and the characteristics of conventional purification and crystallization processes. Paclitaxel (NSC 125973, better known as taxol®, a trademark of the Bristol-Myers Squibb Company), an anticancer drug originally derived from the western yew *Taxus brevifolia,* is an example of such a compound. This material typically gives needle-like crystals from conventional crystallization (Wani, M. C., Taylor, H. L., Wall, M. E., Coggon, P. and McPhail, A. T., Plant Antitumor Agents. VI. Isolation and Structure of Taxol, A Novel Antileukemic and Antitumor Agent From *Taxus brevifolia, Journal of American Chemical Society,* 93:2325–2327, 1971).

Paclitaxel is a moderately sized molecule (MW=854, 113 atoms) with a complex structure that may hinder crystallization by conventional means or otherwise. As used herein, the term complex refers to molecules having approximately twenty-five or more atoms, and which are not comprised entirely of repeating subunits. For example, proteins are considered to have complex structure but polyethylene is not. The structure of paclitaxel is represented by the formula below:

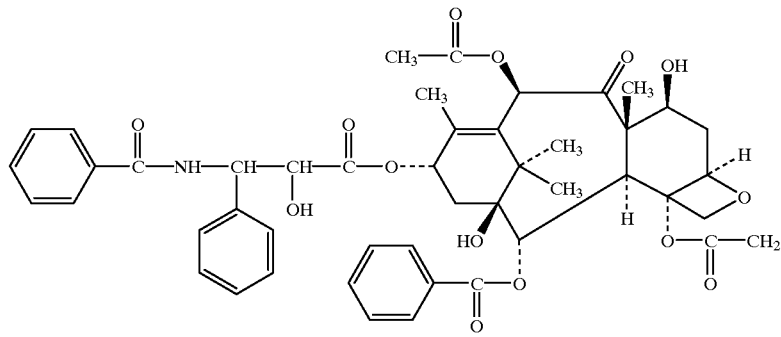

Many other natural therapeutics of current interest likewise possess complex structures, e.g. bryostatin 1 (MW= 905, 132 atoms). The structure of bryostatin 1 is represented by the formula below:

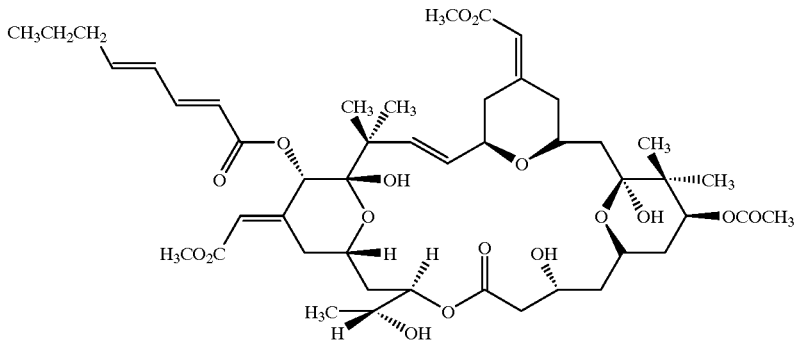

A need exists for a process which can produce large, highly ordered crystals of complex molecules.

SUMMARY OF THE INVENTION

The present invention features methods of forming large sized crystals and the crystal compositions so formed. One embodiment of the present method for forming crystals comprises the steps of providing a compound of 90–100% purity, which compound is selected from the group of complex compounds having 25 or more atoms. The compound is dissolved in a first conventional solvent to form a first solution. The first solution is combined with an antisolvent comprising a critical, supercritical or near critical fluid, with which it is miscible, to form a solution supersaturated in said compound. Typical supersaturation ratios may be in the range of 10–100. The compound is allowed to precipitate out of the saturated solution as crystals, and the crystals are harvested.

In an alternative embodiment, the first solvent may be a critical, supercritical or near critical fluid while the antisolvent may be a conventional solvent. In another alternative embodiment, both the first solvent and the antisolvent may be critical, supercritical or near critical fluids.

Preferably the critical, supercritical or near critical fluid is a supercritical fluid. In the supercritical region, fluid density may be varied in a continuous manner without the occurrence of a liquid-vapor phase transition. This may be effected by changing either the temperature or pressure, providing a means of "fine tuning" intermolecular interactions, and thus facilitating optimization of various chemical and physical processes. For instance, temperature changes of tens of degrees or pressure changes by tens of atmospheres can cause solubility to change by an order of magnitude or more. This unique feature facilitates solute recovery and the selective fractionation of mixed solutes. In addition to its distinct solubilization characteristics, a supercritical fluid possesses other physicochemical properties that add to its attractiveness as a solvent. A supercritical fluid solvent can exhibit a liquid-like density, and at the same time, gas-like diffusivity and viscosity. The latter increases mass transfer rates, significantly reducing processing times.

Preferably, the fluid in the saturated solution has a concentration which does not exceed the concentration which forms visible crystals immediately upon combining the first solution with the fluid.

Preferably, the compound is allowed to precipitate out of the saturated fluid over a period of time of up to 48 hours.

Preferably, the conventional solvent is selected from the group of solvents consisting of acetone, methanol, ethanol, propanol, butanol, tetrahydrofuran, methylene chloride, chloroform, toluene, dimethylsulfoxide, N, N, dimethylformamide, cyclohexanone, butyrolactone, water and combinations of two or more of this group.

Preferably the supercritical, critical or near critical fluid is selected from the group of gases capable of forming a critical, supercritical or near critical fluid consisting of nitrous oxide, propane and other light alkanes, ethylene and other light alkenes, fluorocarbons, chlorofluorocarbons, and carbon dioxide.

A further embodiment of the present invention comprises paclitaxel having a nondendritic crystal habit. As used herein, the term nondendritic habit refers to crystals with limited needle form or snowflake like form. By way of example, the paclitaxel composition of the present invention is characterized by compact crystals with dimensions of about 400×200×50 microns.

Thus, it has been discovered that normally gaseous materials, when compressed, can provide surprisingly large and well ordered crystals from molecules of complex structure. The invention is also useful as a purification method.

In comparison to conventional techniques, crystals can be obtained that are larger, of uniform and compact shape, have fewer inclusions and are more perfect, making X-ray and neutron crystallographic studies much easier and less time-consuming to carry out. Improved crystal growth will allow a more accurate structure determination of macromolecules, and can aid in elucidating their structure/function relationships. The latter in turn contribute greatly to the knowledge base necessary for modifying natural products to provide different or improved function.

These and other features and advantages will be apparent to those skilled in the art in view of the drawings and detailed description which follow.

DETAILED DESCRIPTION OF THE INVENTION

Figure 1:
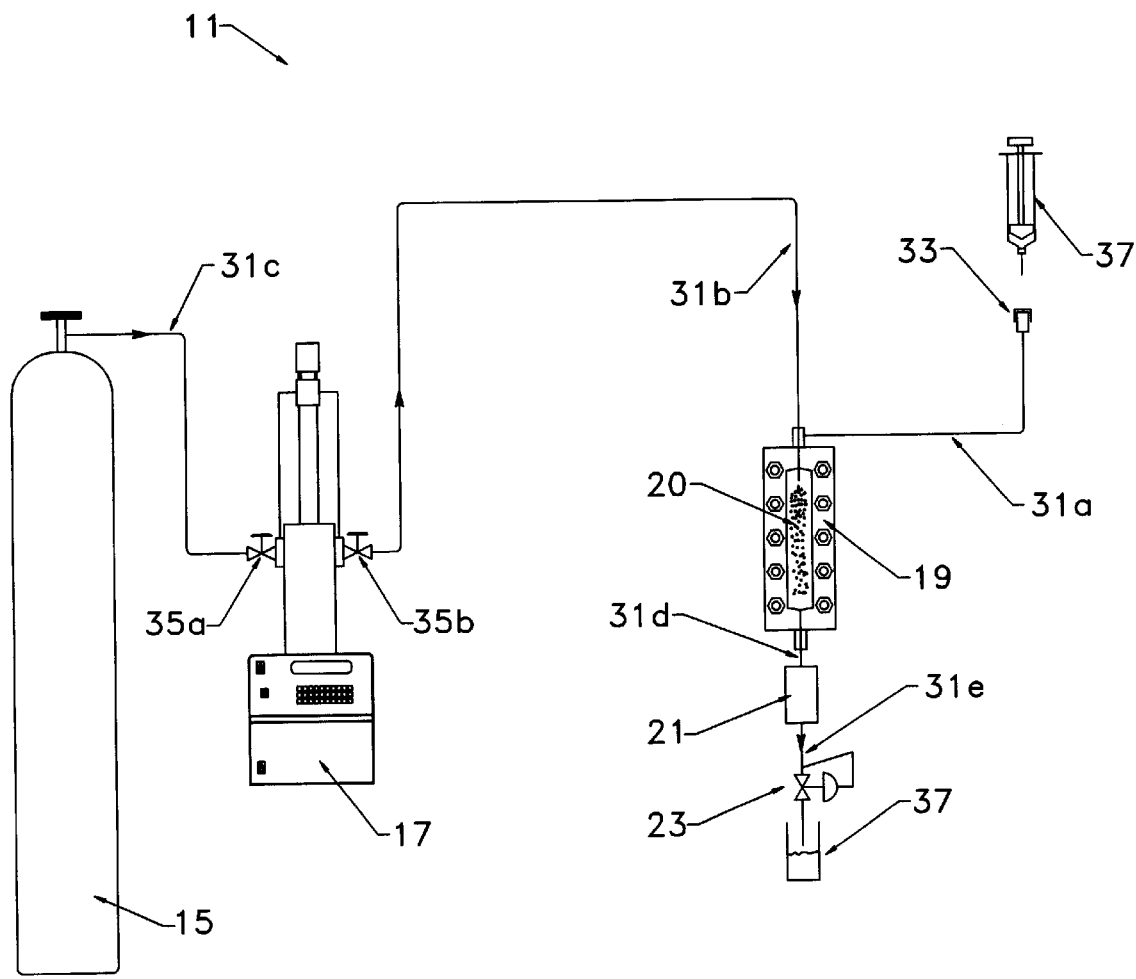
FIG. 1 is a schematic representation of an apparatus utilized for performing embodiments of the present method.

The present invention will be described in detail with respect to methods and compositions which feature paclitaxel. However, the present methods and compositions have broad applications and individuals skilled in the art will recognize the utility of the present invention to any composition in which large well ordered crystals are desired.

One embodiment of the present method for forming crystals comprises the steps of providing a compound of 90–100% purity, which compound is selected from the group of complex compounds having 25 or more atoms. The compound is dissolved in a first conventional solvent to form a first solution. The first solution is combined with an antisolvent comprising a critical, supercritical or near critical fluid, with which it is miscible, to form a solution supersaturated in said compound. Typical supersaturation ratios may be in the range of 10–100. The compound is allowed to precipitate out of the saturated solution as crystals, and the crystals are harvested.

An apparatus for performing embodiments of the present methods, generally designated by the numeral 11, is depicted in FIG. 1. The apparatus comprises the following major elements; a source of critical, supercritical or near critical fluid 15, fluid metering apparatus 17, sight glass vessel 19, filter assembly 21, back pressure regulator 23 and conduits 31. This apparatus 11 is intended to operate at near critical and supercritical pressures and temperatures. The pressure may exceed 3,000 psi. To control the temperature at these pressures, the apparatus may be housed in a temperature controlled environment. Such housing is not depicted in the drawing for purposes of clarity.

A preferred sight glass vessel 19 is a Strahman sight glass vessel. This vessel has a volume of approximately 150 ml. Preferably sight glass vessel 19 is in communication with a fitting 33 via a conduit 31a. Fitting 33 is capable of receiving a needle 37. Needle 37 contains the sample which will be loaded into sight glass vessel 19 through fitting 33 and conduit 31a. Sight glass vessel 19 has a glass port 20 for viewing the sample.

Sight glass vessel 19 is in communication with a source 15 of critical, supercritical or near critical fluid by conduits 31b and 31c. Fluid metering apparatus 17, in communication with source 15 and sight glass vessel 19, is interposed between conduit 31b and conduit 31c. Fluid metering apparatus 17 controls the amount of fluid entering sight glass vessel 19 by valves 35a and 35b. A preferred fluid metering means 17 comprises a syringe pump.

Sight glass vessel 19 is in communication with filter assembly 21 via conduit 31d. Filter assembly 21 is capable of capturing crystals of the desired compound which precipitate during the process and are carried from sight glass vessel 19 during the removal of fluid and solvent.

Filter assembly 21 is in communication with back pressure regulator 23 via conduit 31e. Back pressure regulator 23 controls the pressure in the apparatus 11. Back pressure regulator 23 is capable of venting solvent and fluid to collection vessel 37.

In operation, the solubility of the compound, for which crystals are desired, is determined in the solvent and critical, supercritical or near critical fluid. Preferably, the solvent is selected from the group of solvents consisting of acetone, methanol, ethanol, propanol, butanol, tetrahydrofuran, methylene chloride, chloroform, toluene, dimethylsulfoxide, N, N, dimethylformamide, cyclohexanonone, butyrolactone, water and combinations of two or more of this group. Preferred solvents comprise methanol, ethanol and acetone. The solvent is chosen on the basis of solvation properties with respect to the compound. Preferred solvents exhibit decreased properties of solvation as mixtures with a selected critical, supercritical or near critical fluid.

Approximately 100–200 mg of the compound is dissolved in approximately 10–20 ml of the selected solvent. This solution is drawn into a syringe and needle 37, and injected into fitting 33. The solution flows into sight glass vessel 19 through conduit 31a. Fitting 33 is then capped. Back pressure regulator 23 is closed and sight glass vessel 19, filter 21, and conduits 31b–e are brought to a pressure of approximately 800 psi with fluid from the source 15.

The critical, supercritical or near critical fluid from the source 15 is added in increments of 20–80 psi by fluid metering means 17. Fluid is added until the concentration of the fluid exceeds the solubility of the compound in the mixture of solvent and fluid by a factor of 20–50, with no crystals visible in the sight glass vessel 19.

The sight glass vessel 19 is allowed to develop crystals over a period of time of up to 48 hours. Crystals should appear on the sight glass within 24 hours. Additional fluid may be added to the system after 6–24 hours to force further crystallization.

The solvent rich layers are flushed out with critical, super critical or near critical fluid. Back pressure regulator is backed down slowly to ambient, leaving crystals within the sight glass vessel 19 and on the filter 21. The solvent is collected in collection vessel 37 and the crystals harvested. The crystals formed by the present method are large and compact.

The invention may be more fully understood with reference to the following examples which describe methods of the present invention with respect to two preferred compounds.

EXAMPLE 1

Crystallization of Paclitaxel from Conventional Solvents

This example describes a typical conventional process for the crystallization of paclitaxel. In this process, the paclitaxel is first crystallized from methanol/water to remove water-soluble impurities. This is followed by crystallization from acetone/hexane to remove hexane soluble impurities. The technique is similar for both systems.

In the methanol/water system, paclitaxel is dissolved at a concentration of 5–10 grams paclitaxel/liter methanol. The solution is warmed to 50° C. and water is slowly added. When paclitaxel crystals begin to form, water addition is terminated and the solution is allowed to cool slowly. The crystal crop is assayed and recrystallized until a specified purity has been obtained. When the crystals are sufficiently pure, they are partially dried for the next phase.

The purified and partially dried crystals from the methanol/water crystallization are dissolved in acetone at the 10–20 grams/liter level. The solution is warmed to 45° C. and 1.5 volumes of hexane are slowly added. Heating of the solution is continued and the hexane/water/acetone azeotrope is allowed to remove residual water and excess acetone. When sufficient acetone has been removed crystallization will begin. The solution is allowed to cool slowly to recover the paclitaxel crystals. Thus, both portions of this conventional method involve shifting the chemistry and temperature of the medium in combination. Photomicrographs (100×) of the paclitaxel crystals produced by this technique typically exhibit a needle-like habit.

Numerous variations of conventional crystallization have been carried out, including conditions which would be expected to form large crystal sizes. The result, however, has always been small crystal size and needle-like habit. This finding is consistent with the results of Wani, et al. (1971).

EXAMPLE 2

Solubility of Paclitaxel in CO2-cosolvent Mixtures

To establish parameters for anti-solvent crystallization using compressed fluids, the solubility of paclitaxel was determined in mixtures of CO2-acetone and CO2-methanol using an ISCO SFX 2–10 extraction apparatus. (Cosman, M., Crystallization and Purification of Natural Product Therapeutics, SBIR Phase I Final Report to National Science Foundation, Grant No.: III-9361708, Aug. 30, 1994). These results are shown in Tables 1 and 2, respectively. Experimental conditions were 2000 psig and 25° C. At these conditions both acetone and methanol are miscible with CO2, so that a single liquid phase is formed.

As shown in the tables for either system, increasing the CO2 anti-solvent content will eventually lead to precipitation of paclitaxel given a sufficient initial concentration. The CO2-acetone system appeared to give more consistent results, and hence was selected for the crystallization study of Example 3. However, the CO2-methanol system should also prove useful in certain applications.

TABLE 1

Solubility of paclitaxel in $CO_2$-acteone.

| Experiment No. | Acetone, volume % | Acetone, mole % | Solubility, mg/liter |
| --- | --- | --- | --- |
| 40 | 0 | 0 | 39 |
| 31 | 9 | 6 | 59 |
| 35 | 10 | 7 | 32 |
| 33 | 15 | 11 | 90 |
| 34 | 20 | 15 | 233 |
| 36 | 30 | 23 | 1738 |
| 37 | 40 | 31 | 9750 |

TABLE 2

Solubility of paclitaxel in $CO_2$-methanol.

| Experiment No. | Methanol, volume % | Methanol, mole % | Solubility, mg/liter |
| --- | --- | --- | --- |
| 40 | 0 | 0 | 39 |
| 45 | 5 | 6 | <25 |
| 46 | 10 | 12 | 1207 |
| 48 | 15 | 18 | 1601 |
| 47 | 20 | 24 | 1912 |

EXAMPLE 3

Crystallization of Paclitaxel from CO2-acetone

The apparatus shown in FIG. 1 was utilized to perform the method of crystallization with liquid $CO_2$ at 25° C. The heart of the apparatus is a Strahman sight glass vessel 19 rated at 2000 psig at ambient temperatures. This windowed vessel has a volume of approximately 150 cc. A solution of 150 mg of approximately 97% pure paclitaxel, which had previously been subjected to the conventional crystallization process described in Example 1, was dissolved in 15 cc of acetone and loaded into the sight glass vessel 19 at ambient conditions through fitting 33 using syringe 37. The system was then equilibrated with $CO_2$ from source 15 to a pressure of approximately 800 psig, by opening valves 35a and 35b of fluid metering means 17 and closing back pressure regulator 23. Next, carbon dioxide was added in 50 psi increments using the fluid metering means 17. After reaching a pressure of 1950 psig, with an acetone mole fraction of 7% and no crystals visible, the apparatus 11 was left overnight. According to Table 1, only about 5 mg out of the 150 mg of paclitaxel should have been soluble under these conditions, so that the supersaturation factor was about 30.

The next day, crystals were observed, clustered on the internal stainless steel surfaces of the sight vessel 19. Some of these crystals were dendritic ("snowflake-like") in form. The apparatus was allowed to sit for another day before the crystals were harvested. This was done by pumping additional pure $CO_2$ through the system with the back pressure regulator set at approximately 2000 psig. All of the acetone rich layer was flushed out by continued addition of $CO_2$ at 2000 psig. The back pressure regulator was then backed down gradually to ambient, leaving paclitaxel crystals in the sight glass and on the filter 16. The acetone was collected in beaker 20.

The crystals were harvested by disassembling the sight glass and scraping the internal surfaces. One of the surprises in this experiment was the significantly improved morphology of the new crystals as compared to crystals formed by using the conventional method of Example 1. Photomicrographs (100×) of some of the crystals formed by the present method are strikingly different compared with the conventional crystals shown at the same magnification. By conventional processes, the crystal form was needles, making the material difficult to weigh out and handle. The $CO_2$-acetone crystals are much larger, with dimensions of about 400×200×50 microns and a greater degree of symmetry. Photomicrographs of the crystals of the present invention typically reveal a compact structure, i.e., lack of void spaces or needle-like or dendritic habit. Such crystals were chromatographically analyzed and retained the 97% purity of the conventional crystal starting material.

The high quality of the crystals formed in the process of the present invention may aid chemical investigation of new compounds by facilitating the formation of crystals large enough for X-ray crystallography or other structural investigation techniques. X-ray work requires crystals with dimensions of approximately 1–2 mm. Neutron diffraction requires larger crystals, ideally ~3–4 mm. Frequently, biological crystals deteriorate in the X-ray beam, requiring a new crystal to be mounted every few hours or days. This means that a steady supply of new crystals is required to complete the study. Data collection may take weeks or even months for large molecules. Thus, the present invention has particular utility in the determination of molecular structure.

EXAMPLE 4

Crystallization of Bryostatin 1

This example describes the method of the present invention with respect to the compound bryostatin 1. The apparatus shown in FIG. 1 would be utilized to perform the method of crystallization with liquid $CO_2$ at 25° C. Sight glass vessel 19 rated at 2000 psig at ambient temperatures has a volume of approximately 150 cc. A solution of 150 mg of approximately 97% pure bryostatin 1, which had previously been subjected to the conventional crystallization process, would be dissolved in 15 cc of acetone and loaded into the sight glass vessel 19 at ambient conditions through fitting 33 using syringe 37. The system would be equilibrated with $CO_2$ from source 15 to a pressure of approximately 800 psig, by opening valves 35a and 35b of fluid metering means 17 and closing back pressure regulator 23. Next, carbon dioxide would be added in 50 psi increments using the fluid metering means 17. After reaching a pressure, determined by the solubility of bryostatin 1 in the solution with carbon dioxide, and no crystals visible, the apparatus 11 would be left overnight. Preferably, the supersaturation factor would be in the range of 20 to about 50.

The next day, crystals should be observed, clustered on the internal stainless steel surfaces of the sight glass vessel 19. The apparatus would be allowed to sit for another day before the crystals would be harvested. Additional pure $CO_2$ would be pumped through the system with the back pressure regulator 23 set at approximately 2000 psig. All of the acetone rich layer would be flushed out by continued addition of $CO_2$ at 2000 psig. The back pressure regulator 23 would be then backed down gradually to ambient, leaving bryostatin 1 crystals in the sight glass vessel 19 and on the filter 16. The acetone would be collected in beaker 20. The crystals would be harvested by disassembling the sight glass vessel 19 and scraping the internal surfaces.

While the invention has been described in terms of particular embodiments, it will be appreciated by those skilled in the art that various modifications may be practiced without departing from the spirit and scope of the invention. For example, the invention may be practiced with compressed gases, supercritical fluids, or liquefied gases. In addition, the driving force for precipitation may be a combination of solvent chemistry shift and thermal shift. Furthermore, as solvent power with compressed fluids may be adjusted by the pressure level, chemistry shift may also be used in combination with pressure shift, or in combination with both pressure and thermal shift.

What is claimed is:

1. A method for forming crystals of compositions selected from the group consisting of taxoids and brystatins comprising the steps:
   (a.) providing a compound of 90–100% purity selected from the group consisting of taxoids and brystatins, and dissolving said compound in a solvent to form a first solution,
   (b.) combining said first solution with a critical, supercritical or near critical fluid to form a second solution comprising said fluid, solvent and said compound, said second solution having a concentration of said compound 5 to 1000 times the solubility of said compound; and,
   (c.) allowing said compound to precipitate out of said second solution as crystals with a minimum dimension of 25 to 100 microns and harvesting the crystals formed wherein said crystals do not exhibit needle-like habit.

2. The method of claim 1 wherein the concentration of said compound in the second solution does not exceed the concentration of said compound which immediately forms visible crystals upon combining said first solution with said fluid.

3. The method of claim 1 wherein said compound is allowed to precipitate out of said second solution over a period of time of up to 48 hours.

4. The method of claim 1 wherein said solvent is selected from the group of solvents consisting of acetone, methanol, ethanol, propanol, butanol, tetrahydrofuran, methylene chloride, chloroform, toluene, dimethylsulfoxide, N, N, dimethylformamide, cyclohexanone, butyrolactone, water and combinations of two or more of this group.

5. The method of claim 1 wherein said supercritical, critical or near critical fluid is selected from the group of gases capable of forming a critical, supercritical or near critical fluid consisting of nitrous oxide, propane and other light alkanes, ethylene and other light alkenes, fluorocarbons, chlorofluorocarbons, and carbon dioxide.

6. The method of claim 1 wherein said solvent is a supercritical, critical or near critical fluid.

7. A method for forming crystals of compositions selected from the group consisting of taxoids and brystatins comprising the steps:
   (a.) providing a compound of 90–100% purity, said compound selected from the group consisting of taxoids and brystatins and dissolving said compound in a solvent to form a first solution,
   (b.) combining said first solution with a solvent to form a second solution comprising said fluid, solvent and said compound, said solvent selected from the group of solvents consisting of acetone, methanol, ethanol, butanol, tetrahydrofuran, methylene chloride, chloroform, toluene, dimethylsulfoxide, N, N, dimethylformamide, cyclohexanone, butyrolactone, water and combinations of two or more of this group;
   (c.) said second solution having a concentration of said compound 5 to 1000 times the solubility of said compound; and,
   (d.) allowing said compound to precipitate out of said second solution as crystals with a minimum dimension of 25 to 100 microns and harvesting the crystals formed wherein said crystals do not exhibit needle-like habit.

8. A method for forming paclitaxel crystals comprising the steps:
   (a.) providing paclitaxel of 90–100% purity, and dissolving said paclitaxel in a solvent to form a first solution,
   (b.) combining said first solution with a critical, supercritical or near critical fluid to form a second solution comprising said fluid, solvent and said paclitaxel, said second solution having a concentration of paclitaxel 5 to 1000 times the solubility of paclitaxel; and,
   (c.) allowing paclitaxel to precipitate out of said second solution as crystals with a minimum dimension of 25 to 100 microns and harvesting the crystals formed wherein said crystals do not exhibit needle-like habit.

9. The method of claim 8 wherein said critical, supercritical or near critical fluid is carbon dioxide.

10. The method of claim 9 wherein said carbon dioxide is added in 25–75 psi increments.

11. The method of claim 9 wherein said carbon dioxide is added to a concentration which exceeds the solubility of paclitaxel by a factor of approximately 30.

12. The method of claim 8 wherein said solvent is acetone.

13. The method of claim 8 wherein said solvent is flushed from the crystals with the critical, supercritical or near critical fluid prior to harvesting.

14. A method for forming paclitaxel crystals comprising the steps:
   (a.) providing paclitaxel of 90–100% purity, and dissolving said paclitaxel in a solvent consisting essentially of acetone to form a first solution,
   (b.) combining said first solution with a critical, supercritical or near critical fluid to form a second solution comprising said fluid, solvent and said paclitaxel, said second solution having a concentration of paclitaxel 5 to 1000 times the solubility of paclitaxel; and,
   (c.) allowing paclitaxel to precipitate out of said second solution as crystals with a minimum dimension of 25 to 100 microns and harvesting the crystals formed wherein said crystals do not exhibit needle-like habit.

15. The method of claim 14 wherein said fluid is added in increments of 25 to 75 psi.

* * * * *